United States Patent
Miyazaki et al.

(10) Patent No.: US 8,858,201 B2
(45) Date of Patent: *Oct. 14, 2014

(54) FLUID TRANSPORTING DEVICE OF THE PERISTALTIC TYPE WITH A PUSH PIN AND PUSH PLATE ARRANGEMENT

(71) Applicant: Seiko Epson Corporation, Tokyo (JP)

(72) Inventors: Hajime Miyazaki, Matsumoto (JP); Kazuo Kawasumi, Chino (JP); Kenichi Ushikoshi, Shiojiri (JP)

(73) Assignee: Seiko Epson Corporation (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/890,466

(22) Filed: May 9, 2013

(65) Prior Publication Data

US 2013/0243632 A1    Sep. 19, 2013

Related U.S. Application Data

(62) Division of application No. 13/412,066, filed on Mar. 5, 2012, which is a division of application No. 12/617,771, filed on Nov. 13, 2009, now Pat. No. 8,157,546, which is a division of application No. 11/795,994, filed as application No. PCT/JP2006/301398 on Jan. 24, 2006, now Pat. No. 7,950,908.

(30) Foreign Application Priority Data

Jan. 26, 2005 (JP) ................ 2005-017932

(51) Int. Cl.
*F04B 43/12* (2006.01)
*F04B 43/08* (2006.01)
*A61M 5/142* (2006.01)

(52) U.S. Cl.
CPC ......... *F04B 43/1223* (2013.01); *F04B 43/1253* (2013.01); *F04B 43/12* (2013.01); *F04B 43/082* (2013.01); *A61M 5/14232* (2013.01)
USPC ...................................... 417/477.3

(58) Field of Classification Search
CPC .. A61M 5/14228; F04B 43/08; F04B 43/082; F04B 43/12
USPC ........ 417/474, 475, 476, 477.1, 477.2, 477.3, 417/477.4, 477.5, 477.6, 477.7, 477.8, 417/477.9, 477.11, 477.12, 477.13, 477.14; 74/567, 568, 569, 55

See application file for complete search history.

(56) References Cited

U.S. PATENT DOCUMENTS 1,982,603 A * 11/1934 Barbaron .................. 74/55
2,317,344 A *  4/1943 Hood ..................... 290/38 A (Continued)

FOREIGN PATENT DOCUMENTS

DE          2722647 A1   12/1977
DE   10 2005 055 013 B3    3/2007

(Continued)

OTHER PUBLICATIONS

International Search Report for PCT/JP2006/301398, dated Apr. 7, 2006, ISA/JP (in English).

*Primary Examiner* — Nathan Zollinger
(74) *Attorney, Agent, or Firm* — Harness, Dickey & Pierce, P.L.C.

(57) ABSTRACT

A fluid transporting device includes an elastic tube, a tube frame that holds the elastic tube in an arc, a rotary push plate arranged in the arc for facilitating fluid flow inside the elastic tube, and a plurality of push pins disposed between the elastic tube and the center of the arc. Each push pin includes a semispherical end portion that contacts the rotary push plate, a pushing end portion that places a bias on the elastic tube, and adjacent end portions of at least two push pins close the elastic tube when the semispherical end portions are pushed by an outer circumference arc of the rotary push plate.

8 Claims, 7 Drawing Sheets

(56) References Cited

U.S. PATENT DOCUMENTS

| | | |
|---|---|---|
| 3,177,742 A | 4/1965 | Basso |
| 3,630,647 A | 12/1971 | Kochlin |
| 3,738,180 A | 6/1973 | Sola |
| 3,798,982 A | 3/1974 | Lundquist |
| 3,918,854 A | 11/1975 | Catarious et al. |
| 4,178,927 A | 12/1979 | Lundquist |
| 4,535,641 A | 8/1985 | Kriz et al. |
| 4,547,136 A | 10/1985 | Rothstein |
| 4,772,263 A | 9/1988 | Dorman et al. |
| 4,832,584 A | 5/1989 | Nassif |
| 4,893,991 A | 1/1990 | Heminway et al. |
| 5,110,270 A | 5/1992 | Morrick |
| 5,540,561 A | 7/1996 | Johnson |
| 5,575,631 A | 11/1996 | Jester |
| 5,683,233 A | 11/1997 | Moubayed et al. |
| 5,741,125 A | 4/1998 | Neftel et al. |
| 5,791,881 A | 8/1998 | Moubayed et al. |
| 5,924,852 A | 7/1999 | Moubayed et al. |
| 5,945,346 A | 8/1999 | Vanell et al. |
| 6,056,730 A | 5/2000 | Greter |
| 6,106,249 A | 8/2000 | Barak |
| 6,149,508 A | 11/2000 | Vanell et al. |
| 6,164,921 A | 12/2000 | Moubayed et al. |
| 6,371,732 B1 | 4/2002 | Moubayed et al. |
| 6,434,935 B1 | 8/2002 | Rammhofer et al. |
| 6,523,724 B2 | 2/2003 | Paulovich et al. |
| 7,950,908 B2 | 5/2011 | Miyazaki et al. |
| 2004/0007590 A1 | 1/2004 | Hedington et al. |
| 2007/0128060 A1 | 6/2007 | Miyazaki et al. |
| 2007/0154336 A1 | 7/2007 | Miyazaki et al. |
| 2008/0138218 A1 | 6/2008 | Miyazaki et al. |
| 2008/0138222 A1 | 6/2008 | Miyazaki et al. |
| 2008/0304982 A1 | 12/2008 | Miyazaki et al. |
| 2009/0060755 A1 | 3/2009 | Miyazaki |
| 2009/0208350 A1 | 8/2009 | Miyazaki et al. |
| 2010/0074781 A1 | 3/2010 | Miyazaki et al. |

FOREIGN PATENT DOCUMENTS

| | | |
|---|---|---|
| FR | 1430288 | 1/1965 |
| JP | 43-005468 | 3/1968 |
| JP | 49-042505 | 7/1972 |
| JP | 06-007436 | 1/1994 |
| JP | 7-217541 | 8/1995 |
| JP | 08-028452 | 1/1996 |
| JP | 10-507799 | 7/1998 |
| JP | 11-137679 | 5/1999 |
| JP | 11-224868 | 8/1999 |
| JP | 2001-515557 | 9/2001 |
| JP | 2001-523995 | 11/2001 |
| JP | 2004-360667 | 12/2004 |
| SU | 853157 | 8/1981 |

* cited by examiner

FLUID TRANSPORTING DEVICE OF THE PERISTALTIC TYPE WITH A PUSH PIN AND PUSH PLATE ARRANGEMENT

This application is a divisional of U.S. patent application Ser. No. 13/412,066 filed Mar. 5, 2012, which is a divisional of U.S. patent application Ser. No. 12/617,771 filed Nov. 13, 2009, now U.S. Pat. No. 8,157,546 issued Apr. 17, 2012, which is a divisional of U.S. patent application Ser. No. 11/795,994 filed on Sep. 28, 2007, now U.S. Pat. No. 7,950,908 issued May 31, 2011, which is a National Stage of PCT/JP2006/301398 filed Jan. 24, 2006. This application claims the benefit of Japanese Patent Application No. 2005-017932 filed Jan. 26, 2005. The disclosures of the above applications are incorporated herein by reference.

TECHNICAL FIELD

The present invention relates to a fluid transporting device and a fluid transporter provided with the fluid transporting device.

BACKGROUND ART

In the prior art, as a first conventional technique, there is known a tube pump (JP-A-10-220357) as a fluid transporting device of a writhing type, in which a tube for feeding a fluid is interposed between a plurality of rollers mounted on a concentric circle of the circumferential edge portion of a rotor and a tube receiving member, so that the rollers are caused to push the tube sequentially by rotating the rotor thereby to feed the fluid.

As a second conventional technique, moreover, there is known a fluid transporting device of a writhing type (U.S. Pat. No. 3,177,742), in which a tube for feeding a fluid is interposed, as in the aforementioned first prior art, between a plurality of rollers mounted on the circumferential edge portion of a rotor and two backings, so that the rollers are caused to push the tube sequentially by rotating the rotor thereby to feed the fluid. This fluid transporting device is constituted such that a motor module for rotating the rotor is laid over a rotor unit.

In the both inventions of the first prior art and the second prior art, however, the rotors rotate while pressing the tube directly by the rollers thereby to transport the liquid. It is, therefore, thought that the fluid feeding portion of the tube (or the internal diameter of the tube) is varied from the initial size as a result that the tube is stretched in the rotating direction of the rotor, so that the fluid flow rate changes thereby to make it difficult to keep the flow rate stably.

Moreover, the aforementioned first prior art is constituted such that the housing includes the fluid transporting device, a drive control circuit, a display unit and a control unit, thereby to make the size reduction difficult.

On the other hand, the aforementioned second prior art is constituted such that the motor module is laid over the roller unit, thereby to raise a problem that the thickness reduction is difficult.

The present invention has been conceived to solve the aforementioned problems, and has an object to provide both a thin, small fluid transporting device, which can continue a stable flow rate, and a fluid transporter which is provided with the fluid transporting device.

DISCLOSURE OF THE INVENTION

According to the invention, there is provided a fluid transporting device characterized: by comprising: a tube having an elasticity; a tube frame having a tube guide wall for mounting said tube in an arcuate shape; a rotary disc arranged on the inner side of said tube; a plurality of push pins arranged radially between said tube and said rotary disc; and a plurality of rollers arranged on the upper face of said rotary disc at an equal interval on a concentric circle with respect to the center of rotation of said rotary disc; in that the arcuate center of said tube guide wall, the center of rotation of said rotary disc and the radial center of said push pins are aligned with each other; and in that said rollers push said push pins sequentially to feed the fluid from the fluid inlet side to the outlet side.

According to this invention, the tube is pressed substantially at right angles by the push pins so that the tube is hardly stretched so that the internal diameter (or the fluid feeding portion) of the tube does not vary, so that a stable fluid rate can be obtained.

Because of the structure for the rotary pressure mechanism to push the push pins, moreover, the flow rate can be freely adjusted by setting the number and stroke of the push pins arbitrarily. It is, therefore, possible to provide a fluid transporting device of a desired flow rate easily.

The rollers are rotated backward of the rotating direction of the rotary disc by the frictional force between the roller and the push pin. As a result, the frictional resistance can be lowered to reduce the driving force of the rotary disc. The torque to be generated by a motor acting as the drive source of the rotary disc may be low, as will be described in detail in the later-described modes of embodiment, so that the size reduction can be made to reduce the size of the fluid transporting device.

Moreover, the invention is characterized in that at least one of said push pins closes said tube.

According to this structure, when the fluid transporting device is run, at least one push pin closes the tube so that the fluid can be continuously fed.

Even when the operation is interrupted, moreover, the tube is closed at its one portion so that the fluid can be prevented from flowing out. This can enhance the safety, in case the fluid is such one of chemicals that its safety has to be considered.

According to the invention, there is provided a fluid transporter characterized in that a fluid transporting device characterized: by comprising: a tube having an elasticity; a tube frame having a tube guide wall for mounting said tube in an arcuate shape; a rotary disc arranged on the inner side of said tube; a plurality of push pins arranged radially between said tube and said rotary disc; and a plurality of rollers arranged on the upper face of said rotary disc at an equal interval on a concentric circle with respect to the center of rotation of said rotary disc; in that the arcuate center of said tube guide wall, the center of rotation of said rotary disc and the radial center of said push pins are aligned with each other; and in that said rollers push said push pins sequentially to feed the fluid from the fluid inlet side to the outlet side, and a fluid storing container for containing a fluid are made to communicate with each other by said tube.

The fluid transporting device of the aforementioned structure is adopted according to this invention, so that the aforementioned effects can be obtained. At the same time, the fluid transporting device and fluid storing container are made to communicate by the tube. As a result, the fluid storing container can be easily replaced so that its handling is facilitated and so that the fluid transporting device can be repeatedly used for economic effects.

Moreover, a fluid transporter of the invention is characterized in that said fluid transporting device and said fluid storing container are formed in parallel in a planar direction in a casing.

According to this structure, the fluid transporting device and the fluid storing container are arranged not to overlap so that they can be reduced in size. Moreover, the casings for the fluid transporting device and the fluid storing container can be made single to reduce the cost.

Moreover, the fluid transporter is characterized: by comprising an opening for producing communication between the inside and the outside of said fluid storing container; and in that an air-permeable film is mounted on said opening.

The fluid storing container is sealed not to leak the fluid. When the fluid transporting device is driven to feed the fluid, the fluid storing container may become negative relative to the ambient pressure (or the atmospheric pressure) thereby to obstruct the flow of the fluid. By sealing the opening with the air-permeable film, therefore, the inside of the fluid storing container can be set to a pressure equivalent to the atmospheric level so that the feed of the fluid can be smoothed.

INDUSTRIAL APPLICABILITY

The fluid transporting device and the fluid transporter of the invention can be mounted inside or outside of a variety of machine apparatus so as to transport a fluid such as water, brine, chemicals, oils, aromatic liquids, ink or gases. Moreover, the fluid transporter can be utilized by itself for feeding and supplying the aforementioned fluid, but should not be limited thereto.

BEST MODE FOR CARRYING OUT THE INVENTION

A fluid transporting device according to the invention and a fluid transporter having the fluid transporting device are described in the following. Here, a mode of embodiment to be described in the following presents only one mode of embodiment, to which the invention should not be limited.

At first, the description is made on Mode of Embodiment 1 of the invention.

Figure 1:
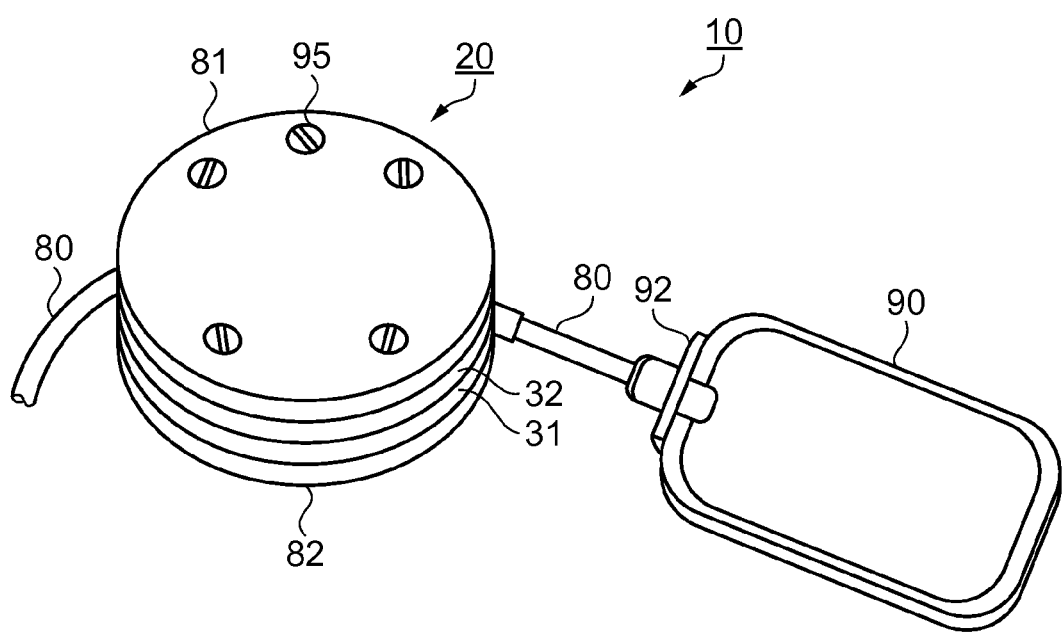
FIG. 1 is a perspective view showing the appearance of a fluid transporter according to Mode of Embodiment 1 of the invention.
Figure 2:
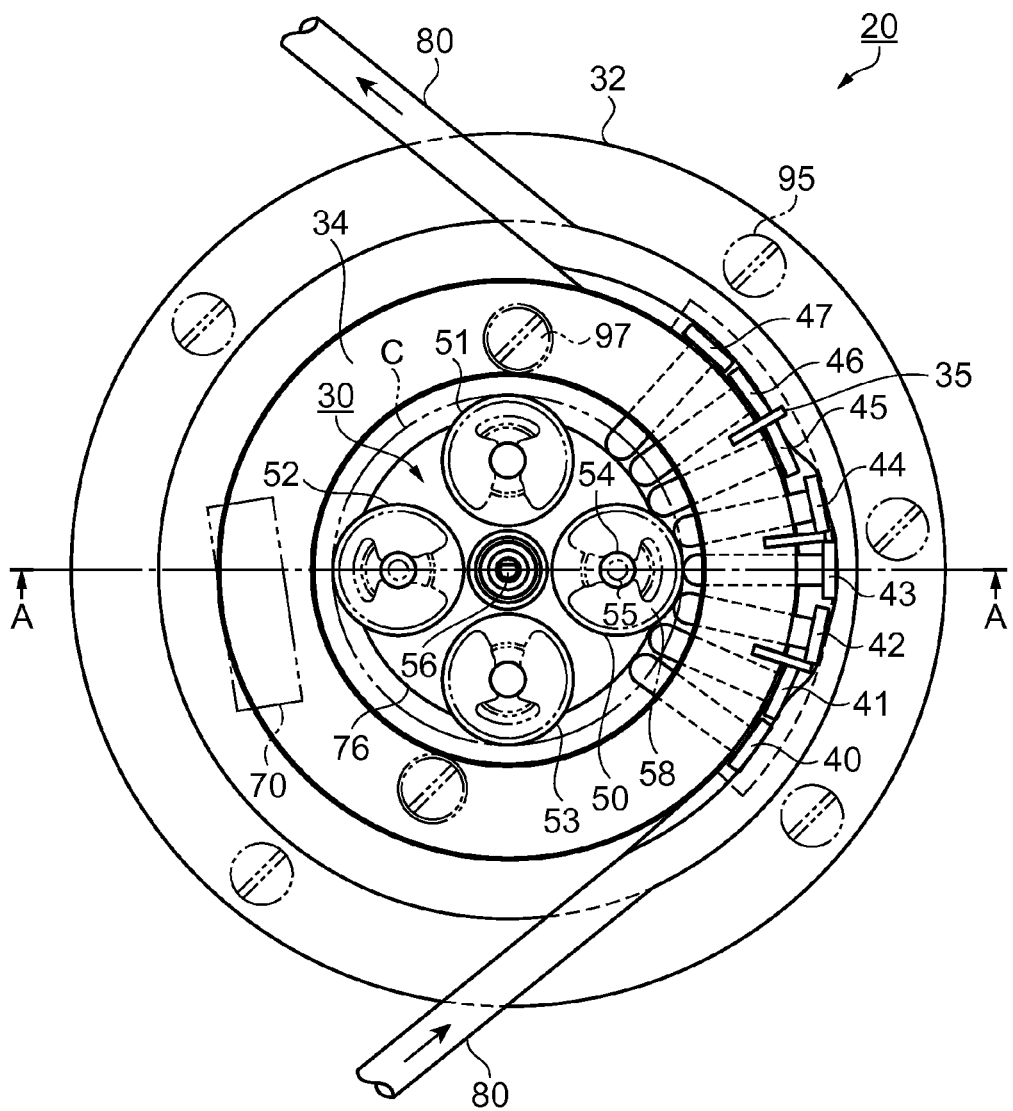
FIG. 2 is a top plan view showing a fluid transporting device according to Mode of Embodiment 1 of the invention.
Figure 3:
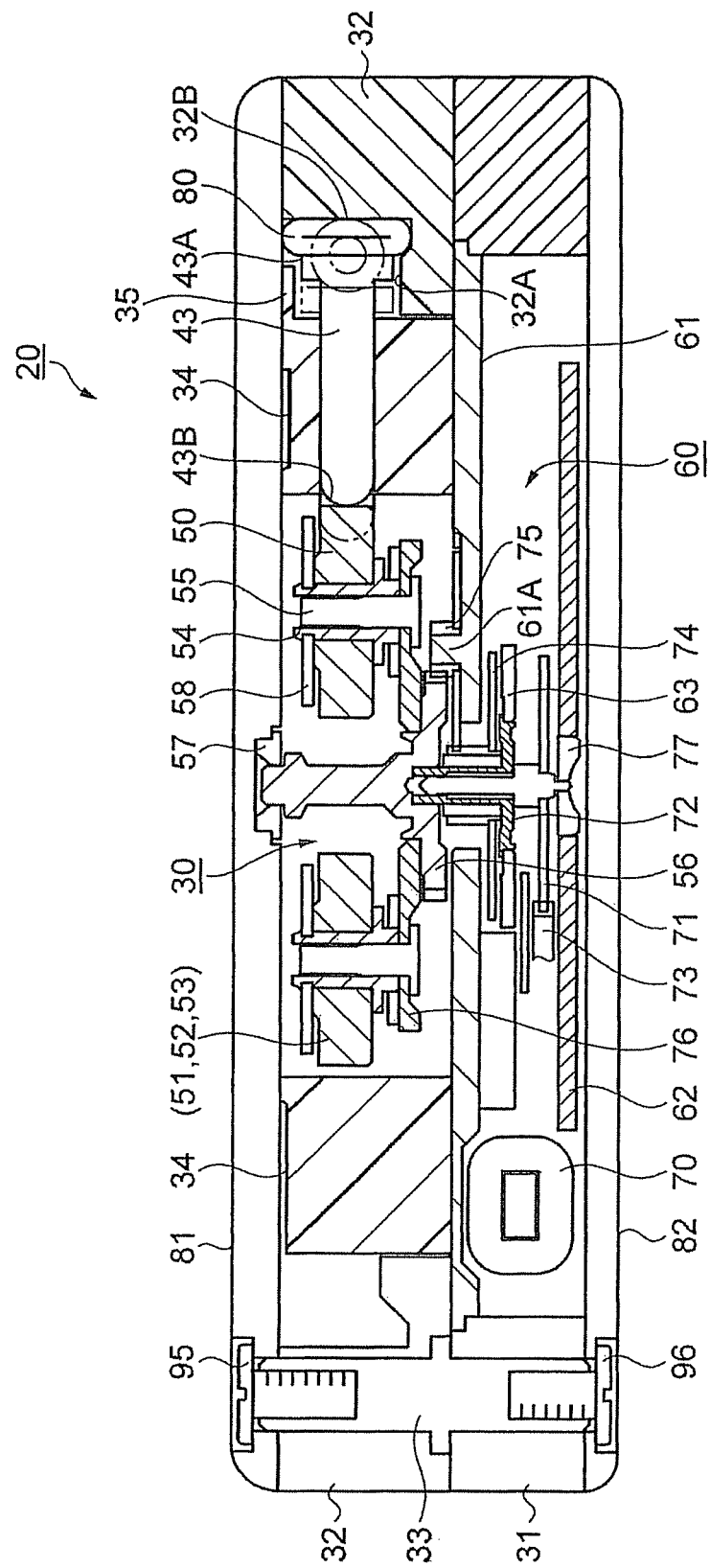
FIG. 3 is a sectional view showing a fluid transporting device according to Mode of Embodiment 1 of the invention.

FIG. 1 to FIG. 3 show the fluid transporter and the fluid transporting device according to Mode of Embodiment 1.

FIG. 1 is a perspective view showing a constitution of the fluid transporter of Mode of Embodiment 1. In FIG. 1, a fluid transporter 10 is constituted of a fluid transporting device 20 for transporting a fluid by writhing motions, and a pack-shaped fluid storing container 90 for storing the fluid. Moreover, the fluid transporting device 20 and the fluid storing container 90 are made to communicate with each other by a tube 80.

The fluid storing container 90 is made of a flexible synthetic resin and formed, in this mode of embodiment, of a silicone-family resin. The fluid storing container 90 is provided at its one end portion with a tube holding portion 92, in which the tube 80 is so hermetically fixed by means such as a press fit such as solvent weld or adhesion that the fluid may not leak.

Here, the fluid to be employed in the invention includes not only a fluidic liquid such as water, brine, chemicals, oils, aromatic liquids or ink but also gases.

The tube 80 communicates at its one end portion with the inside of the fluid storing container 90, and extends through the fluid transporting device 20 and to the outside of the fluid transporting device 20 so that the fluid stored in the fluid storing container 90 may be transported to the outside by the fluid transporting device 20.

The fluid transporting device 20 is constituted by laying a lower cover 82, a pump unit frame 31, a tube frame 32 and an upper cover 81 sequentially in the recited order and by integrating them by means of fixing screws 95 (although the upper cover fixing screws are shown in FIG. 1). In this fluid transporting device 20, there is housed a rotary pressure mechanism for transporting the fluid.

In case the fluid transporter 10 is mounted in a living body, a material excellent in an organic matching property, such as a synthetic resin of polysulfone or urethane is preferably adopted for the lower cover 82, the pump unit frame 31, the tube frame 32, the upper cover 81 and the fluid storing container 90.

Subsequently, a mechanism for transporting a fluid is described with reference to the drawings.

FIG. 2 is a top plan view showing a mechanism for transporting the fluid of the fluid transporting device 20 according to this mode of embodiment. FIG. 3 is a sectional view showing an A-A section of FIG. 2. Here, FIG. 2 shows the state, in which the upper cover 81 is perspectively shown so as to make the description understandable. In FIG. 2 and FIG. 3, the fluid transporting device 20 is basically constituted of a pump unit 30 as a rotary pressure mechanism for pressure the tube 80 by the writhing motions thereby to transport the fluid, and a pump drive unit 60 for driving the pump unit 30. The pump unit 30 and the pump drive unit 60 are constituted to lie in the sectional direction (as referred to FIG. 3).

At first, the description is made on the structure and the drive of the pump drive unit 60. In FIG. 3, the pump drive unit 60 is provided with a first frame 61 of a plate shape, a second frame 62 and a third frame 63. The spaces between those individual frames are provided with motors and transmission gear trains for applying the drive forces to the pump unit 30, and drive circuits for the drive controls (although both are not shown).

In this mode of embodiment, the motor is exemplified by a step motor adopted in a quartz watch or the like, and a coil block 70 is arranged outside of the pump unit 30. The step motor is provided, although not shown, with a stator magnetically coupled to the coil block 70, and a rotor disposed in the stator. The rotor is rotated on the basis of signals coming from the drive circuit (although not shown). This drive circuit is stored in advance with predetermined drive patterns, so that the step motor is driven by the signals based on the drive patterns.

Although not shown, the drive circuit and a battery as a drive source are arranged in the space which is formed by the first frame 61 and the lower cover 82, and the battery is arranged at a position not to intersect with the coil block 70 and the later-described transmission gears. As described hereinbefore, moreover, the lower cover 82 is fixed by means of fixing screws 96 so that the battery can be easily replaced by removing the lower cover 82.

The rotations of the rotor are reduced to a predetermined reduction ratio by a plurality of not-shown transmission gears and are transmitted to a first transmission gear 71. The first transmission gear 71 is borne between a bearing 77 disposed in the second frame 62 and a second transmission gear shaft 72 embedded in the third frame 63. The rotations of the first transmission gear 71 are transmitted through a third transmission gear 73 (although not shown), a fourth transmission gear 74 and a fifth transmission gear 75 to a rotary disc gear 56 positioned at the center of the pump unit 30.

The fourth transmission gear 74 is loosely fitted on the center stem of the second transmission gear shaft 72, and the fifth transmission gear 75 is loosely fitted on a support pin 61A disposed in the first frame 61.

In the pump drive unit 60, the first frame 61 is fixed in the ring-shaped pump unit frame 31 by the not-shown fixing screws. The second frame 62 and the third frame 63 are fixed at a predetermined spacing by the not-shown fixing screws on the first frame 61. Thus, the pump drive unit 60 is united but for the fifth transmission gear 75. The pump unit 30 is mounted over the pump drive unit 60.

Next, the description is made on the structure of the pump unit 30. As shown in FIG. 2, and FIG. 3, the pump unit 30 is basically constituted of: the rotary disc gear 56 to be rotated by the rotating force transmitted from the pump drive unit 60; a rotary disc 76 to be rotated integrally with the rotary disc gear 56; four rollers 50 to 53 disposed on the upper face of the peripheral edge portion of the rotary disc 76; eight push pins 40 to 47 disposed radially from the rotation center of the rotary disc 76; and the tube 80 for feeding the fluid.

The rotary disc 76 is made of a disc-shaped plate member, which bears the rotary disc gear 56 at its central portion. The rotating force is transmitted to the rotary disc gear 56 from the fifth transmission gear 75, so that the rotary disc 76 rotates on the second transmission gear shaft 72. Into the center hole of the rotary disc gear 56, there is inserted the second transmission gear shaft 72, which bears the rotary disc gear 56 together with a bearing 57 disposed in the upper cover 81.

In the outer circumference portion of the rotary disc 76, there are embedded roller support pins 55. These roller support pins 55 are provided by four in number at an equal distance (on a concentric circle) from the center of rotation of the rotary disc 76 and at an equal interval (of 90 degrees) in a planar direction. The four sets of the structure of the roller support pins 55 and the rollers 50 to 53 are identical so that they are described by way of one set. The roller support pins 55 are press-fitted from the lower side of the rotary disc 76, and a roller shaft 54 is press-fitted into the roller support pin 55 from the opposite side across the rotary disc 76.

Moreover, the roller 50 is fitted on the roller shaft 54, and is retained by a C-ring 58. The roller 50 is loosely fitted on the roller shaft 54 so that it can freely rotate. With a similar structure, the rollers 50 to 53 are also arranged at an equal distance from the center of rotation of the rotary disc 76. Around the outer circumference of the rotary disc 76 having those rollers 50 to 53, there is disposed the ring-shaped slide frame 34.

This slide frame 34 also has its center aligned with the center of rotation of the rotary disc 76, and is precisely regulated by the not-shown positioning member and fixed on the first frame 61 by means of fixing screws 97 (as referred to FIG. 2). In the slide frame 34, there are formed eight holes, which extend therethrough radially of the center from the inner side to the outer side. The push pins 40 to 47 are individually inserted into those holes. The push pins 40 to 47 have sizes set to move in the axial direction. Here, the angle made between the axial center of the push pin 40 and the axial center of the push pin 47 is set to 90 degrees or more.

The push pin 43 is representatively described by way of example, because the push pins 40 to 47 have the identical shapes (as referred to FIG. 3). The push pin 43 has its one end portion formed into a flange-shaped push portion 43A and its other end portion rounded into a semispherical push portion 43B. In this structure, the push portion 43B is pushed by the roller 50 so that the push portion 43A presses the tube 80 onto a tube guide wall 32B thereby to squeeze and feed the fluid. The push pin 43 does not press the tube 80 (as indicated by double-dotted lines in FIG. 3) when it does not contact with the rollers 50 to 53.

Around the outer circumference of the slide frame 34, there is further disposed the ring-shaped tube frame 32. This tube frame 32 has its center aligned like the slide frame 34 with the center of rotation of the rotary disc 76. In the inner circumference portion of the tube frame 32, there is formed a step-shaped tube mounting portion 32A for mounting the tube 80. This tube 80 has its planar position regulated between that tube mounting portion 32A and the push portion 43A of the push pin 43. Within the range where the push pins 40 to 47 are absent, the tube 80 is curved and mounted in the shape shown in FIG. 2 by the (not-shown) tube guide grooves formed in the slide frame 34 and the tube frame 32.

The push pins 40 to 47 are radially extended from the center of rotations of the rotary disc 76, and the tube guide wall 32B for pressing the tube 80 is also formed in a circle concentric to the center of rotations of the rotary disc 76. As a result, the tube 80 is pressed substantially at right angles by the push pins 40 to 47.

The slide frame 34 is provided with a tube holder 35 partially protruding toward the upper face of the tube 80 so that the tube 80 may not float. This tube holder 35 is arranged in plurality (e.g., three in FIG. 2) between the push pins 40 to 47 for pressing the tube 80.

In the fluid transporting device 20 of this embodiment, the aforementioned pump drive unit 60 and the pump unit 30 are overlaid, and a fixing pin 33 borne in the pump unit frame is inserted into the tube frame 32 and the upper cover 81. The pump drive unit 60 and the pump unit 30 are fixed by the fixing screws 95. Moreover, the lower cover 82 is also integrally constituted by fixing it by the fixing screws 96. Subsequently, the feeding actions of the fluid in this mode of embodiment are described with reference to FIG. 2. The rotary disc 76 is rotated by the pump drive unit 60 in the fluid feeding direction (as indicated by the arrow in the drawing), that is, counter clockwise in this mode of embodiment. The description is made by way of the roller 50. Before the outermost circumference portion of the roller 50 intersects the push pin 40, the push pin 40 is in the open states. As the rotary disc 76 rotates, the push pin 40 moves toward the tube 80 from the position, at which the outermost circumference (as indicated by a locus C in the drawing) of the roller 50 contacts with the end portion of the push pin 40, thereby to start the push of the tube 80.

Before the roller 50 contacts with the push pin 40 to start the push, at least the push pin 47 is pushed by the roller 51 thereby to close the tube 80, because the angle between the push pins 40 and 47 is set to 90 degrees or more.

As the rotary disc 76 rotates, moreover, the roller 50 pushes the push pins sequentially in the order of the push pins 41, 42 and 43. At this time, the pushing stroke becomes the maximum when the center of rotation of the rotary disc 76, the center of rotation of the roller and the center line of the push pin make a straight line. After this, the roller gradually leaves the push pin so that the tube 80 is released from the push of the push pins. The motions thus pressing the tube 80 sequentially are called the writhing motions, by which the tube 80 is squeezed to transport the fluid. The device for transporting the fluid by making use of such writhing motions is called the writhing type fluid transporting device.

As the rotary disc 76 thus rotates, the rollers 50 to 53 push the push pins 40 to 47 consecutively. As has been described hereinbefore, the angle made between the push pins 40 and 47 is 90 degrees or more so that one of the push pins closes the tube 80.

Moreover, the rollers 50 to 53 are rotated, when they push the push pins 40 to 47, in the direction backward of the rotating direction of the rotary disc 76, that is, counter-clockwise by the frictional force, so that the frictional forces with the push pins 40 to 47 are reduced.

Here, Mode of Embodiment 1 thus far described exemplifies the structure, which is provided with the four rollers and the eight push pins. Despite of this description, however, the embodiment can select the numbers of rollers and push pins arbitrarily.

According to Mode of Embodiment 1 thus far described, therefore, the push pins 40 to 47 push the tube 80 substantially at right angles so that the tube 80 is not stretched. As a result, the internal diameter (or the feeding portion of the fluid) of the tube 80 does not vary so that a stable flow rate can be achieved.

With the structure in which the push pins 40 to 47 are pushed by the rollers 50 to 53, moreover, the flow rate can be freely adjusted by setting the number and stroke of the push pins arbitrarily to provide the fluid transporting device 20 and the fluid transporter of a desired flow rate easily.

Moreover, the rollers 50 to 53 rotate backward of the rotating direction of the rotary disc 76 when they push the push pins 40 to 47, so that the frictional resistance can be reduced to reduce the driving force of the rotary disc 76, so that the output torque of the motor acting as the drive source of the rotary disc 76 can be lowered to reduce the size. Thus, it is possible to reduce the size of the fluid transporting device 20.

Moreover, the fluid transporting device 20 and the fluid storing container 90 are enabled to communicate by the tube 80, so that the fluid storing container 90 can be easily replaced and handled. Moreover, the fluid transporting device 20 can be repeatedly used to raise the economical advantage.

Here, this Mode of Embodiment adopts such structure when the rollers 50 to 53 are borne on the rotary disc 76 as are inserted on the roller shaft 54 and retained by the C-ring 58. However, it is also possible to adopt the structure, in which the rollers 50 to 53 are directly inserted and borne by the roller support pin 55.

Next, a fluid transporting device according to Mode of Embodiment 2 of the invention is described with reference to the accompanying drawing. Mode of Embodiment 1 thus far described has the structure, in which the push pins are pushed onto the tube 80 by the rollers. On the contrary, Mode of Embodiment 2 is characterized by comprising a rotary push plate 100 in place of the rollers so that the push pins are pushed by the rotations of the rotary push plate 100. Therefore, the description is concentrated on the structure of the rotary push plate 100 while omitting the remaining common portions. The description is made by designating the portions common to Mode of Embodiment 1 by the common reference numerals.

Figure 4:
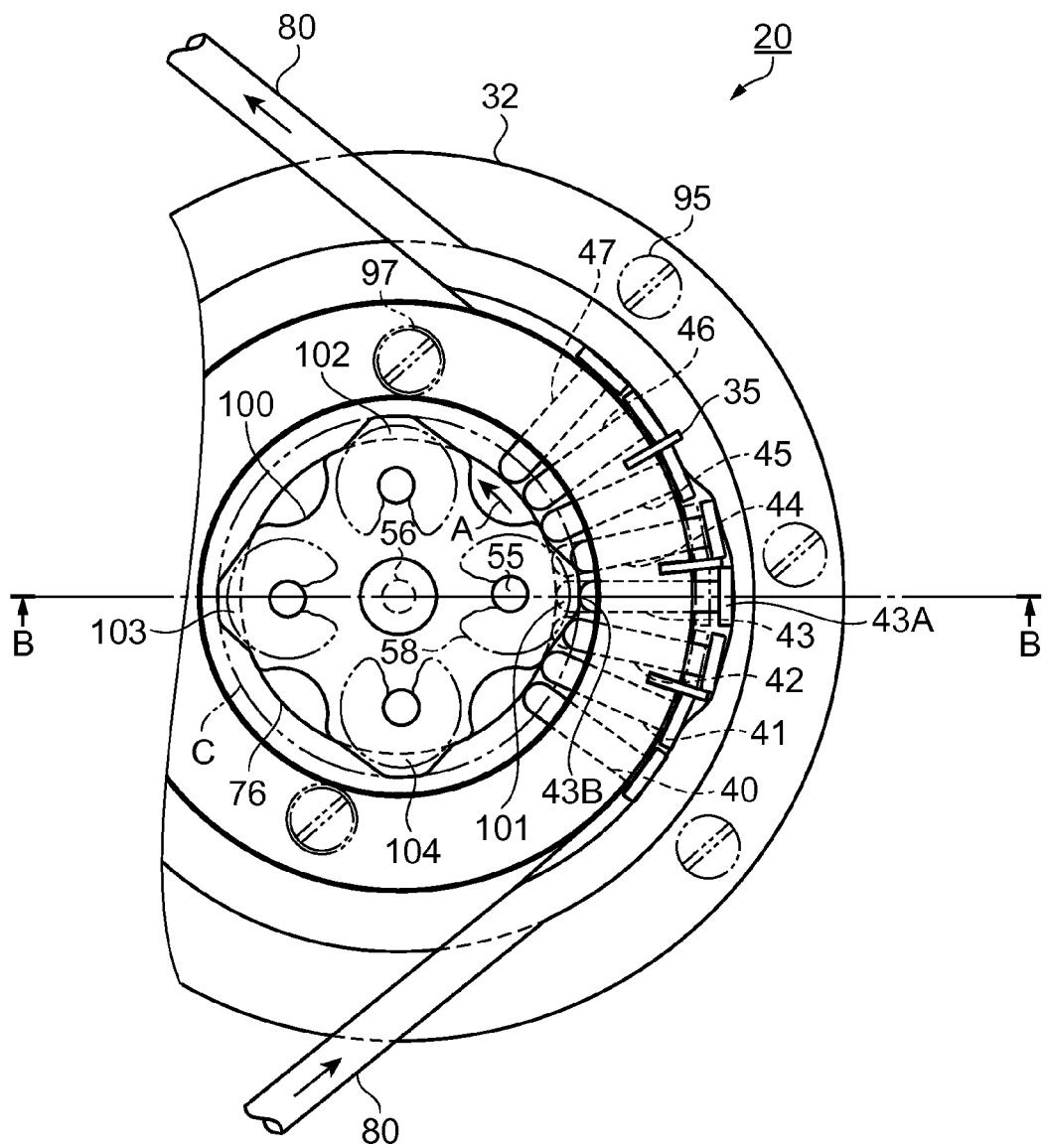
FIG. 4 is a partial top plan view showing a fluid transporting device according to Mode of Embodiment 2 of the invention.
Figure 5:
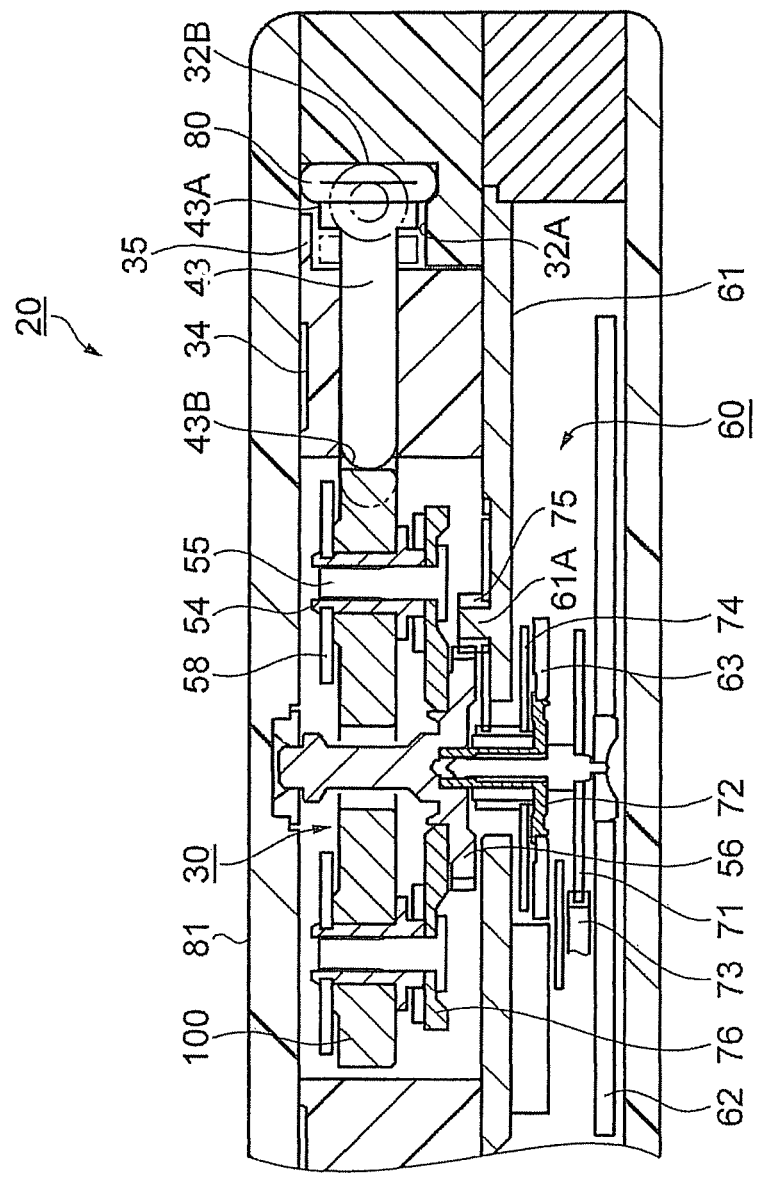
FIG. 5 is a sectional view showing the fluid transporting device according to Mode of Embodiment 2 of the invention.

FIG. 4 is a partial top plan view showing the fluid transporting device 20 according to Mode of Embodiment 2, and FIG. 5 is a sectional view showing a section B-B of FIG. 4.

The description of the structure of the pump drive unit 60 in Mode of Embodiment 2 is omitted because it is identical to that of Mode of Embodiment 1.

Figure 6:
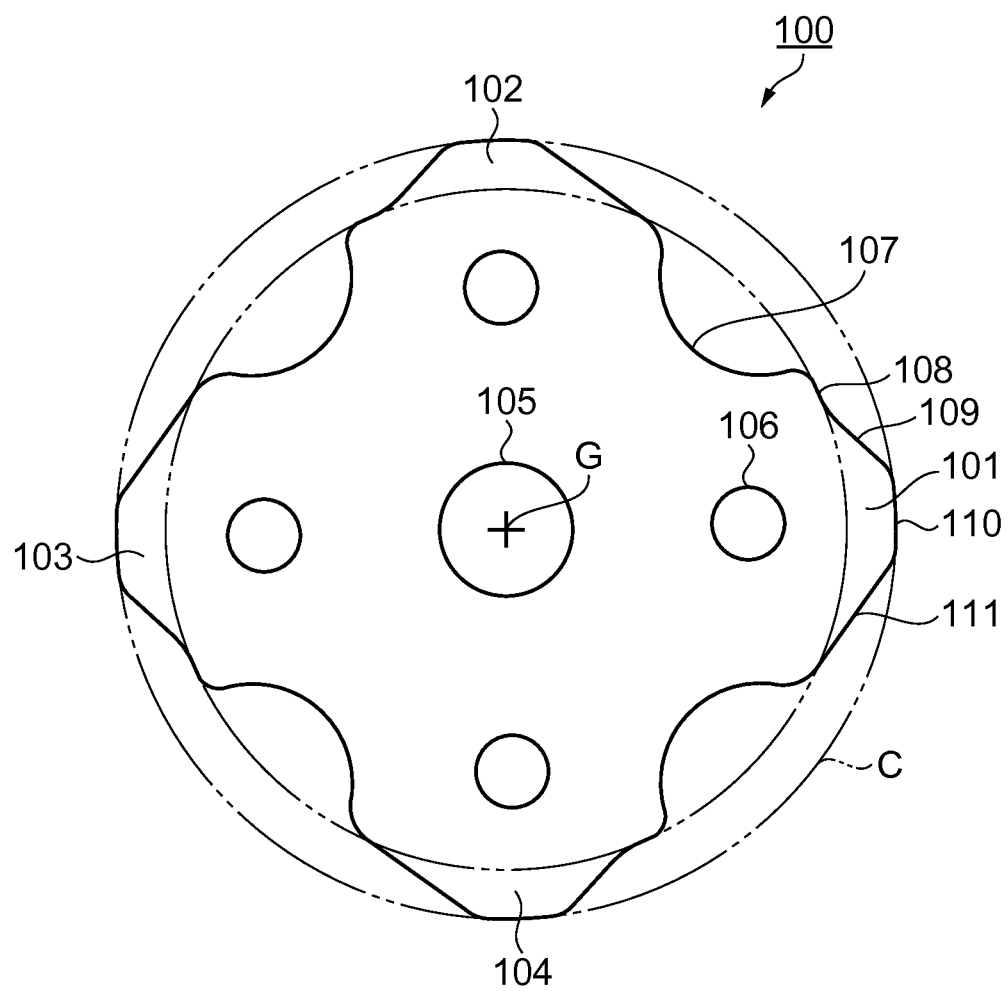
FIG. 6 is a top plan view showing the shape of a rotary push plate according to Mode of Embodiment 2 of the invention.

On the upper face of the rotary disc 76, as shown in FIG. 5 and FIG. 6, there is disposed the rotary push plate 100 (as referred to FIG. 4), which has four protrusions. The rotary push plate 100 is mounted with the four roller support pins 55 as the guide pins, on which the rollers 50 to 53 are fitted and also retained by the C-rings 58, as has been described in Mode of Embodiment 1 (as referred to FIG. 3). The rotary push plate 100 is rotated together with the rotary disc 76 on the center of rotation common to that of the rotary disc 76. The aforementioned four protrusions are push portions 101 to 104 for pushing the push pins 40 to 47. The shape and actions of the rotary push plate 100 are described in detail with reference to FIG. 6.

FIG. 6 is a top plan view showing the shape of the rotary push plate 100. In FIG. 6, the rotary push plate 100 is provided with the four push portions 101 to 104 at its outer circumference. The push portions 101 to 104 are arranged at equal intervals of 90 degrees in the circumferential direction. A hole 105 for inserting the stem portion of the rotary disc gear 56 is opened at the central portion, and four holes 106 for inserting the roller support pins 55 are opened in the outer circumference direction. The push portions 101 to 104 are shaped in point symmetry with respect to the center of rotation G, and the description is made on the push portion 101 by way of example.

An arc 108 is given such a diameter as contacts with or through a slight clearance from the push pins 40 to 47 when the rotary push plate 100 rotates, but it does not push the push pins 40 to 47. When the rotary push plate 100 rotates, a slope 109 gradually begins to push one of the push pins and reaches the maximum pushing stroke at an outer circumference arc 110 (or the rotating locus C of the rotary push plate 100) thereby to close the tube 80. When the rotary push plate 100 then further rotates, it reaches a slope 111 and gradually leaves the push pin so that the tube 80 is opened from the closed state. Then, the fluid flows into the tube 80. Thus, the writhing motions are applied to the push pins 40 to 47 by the rotary push plate 100 thereby to transport the fluid.

Here, a recess 107 is formed between the adjoining push portions thereby to establish the state, in which the push pins 40 to 47 are completely opened. Moreover, the portion between the recess 107 and the arc 108, the portion between the arc 108 and the slope 109, the portion between the slope 109 and the outer circumference arc 110, and the portion between the outer circumference arc 110 and the slope 111 are smoothly rounded to push the push pins 40 to 47 smoothly.

The push pins 40 to 47 have the structure, in which they are moved, when they leave the rotary push plate 100, toward the center of rotation G by the elastic force of the tube 80 thereby to release the closure of the tube 80.

Moreover, the angle made between the push pin 40 and the push pin 47 is set to 90 degrees or more, although described in connection with Mode of Embodiment 1, so that either of the adjoining push portions of the rotary push plate 100 closes the tube 80.

According to Mode of Embodiment 2 thus far described, therefore, the frictional resistance at the time of pushing the push pins 40 to 47 is slightly larger than that of the structure of the foregoing Mode of Embodiment 1 provided with the rollers. However, the single rotary push plate 100 can perform a similar drive thereby to simplify the structure.

If several sets are prepared for the number and shapes of push portions, there can be attained an effect to change the fluid flow rate by changing the rotary push plate for the desired value.

In Mode of Embodiment 2 thus far described (as referred to FIGS. 4 and 5), the rotary push plate 100 is mounted on the roller shaft 54 acting as a guide shaft, but can be directly mounted on the roller support pin 55. Moreover, the object of the invention can also be achieved, even if the four roller shafts or roller support pins are reduced to two (or a pair or) diagonal ones.

Moreover, the rotary push plate 100 and the rotary disc 76 can also be made integral. As in Mode of Embodiment 1, the structure can be provided with the four rotary push plates corresponding to the rollers 50 to 53. In addition, the rotary push plate can also be provided with two or three push portions.

Thus, the structure of the fluid transporting device 20 can be made simpler to reduce the cost.

Next, Mode of Embodiment 3 of the invention is described with reference to the accompanying drawing. Modes of Embodiments 1 and 2 thus far described have the structure, in which the fluid transporter 10 comprises the fluid transporting device 20 and the fluid storing container 90 made separate from each other and made to communicate via the tube 80. On the contrary, Mode of Embodiment 3 is characterized in that the fluid transporting device and the fluid storing container are integrated in a casing.

Figure 7:
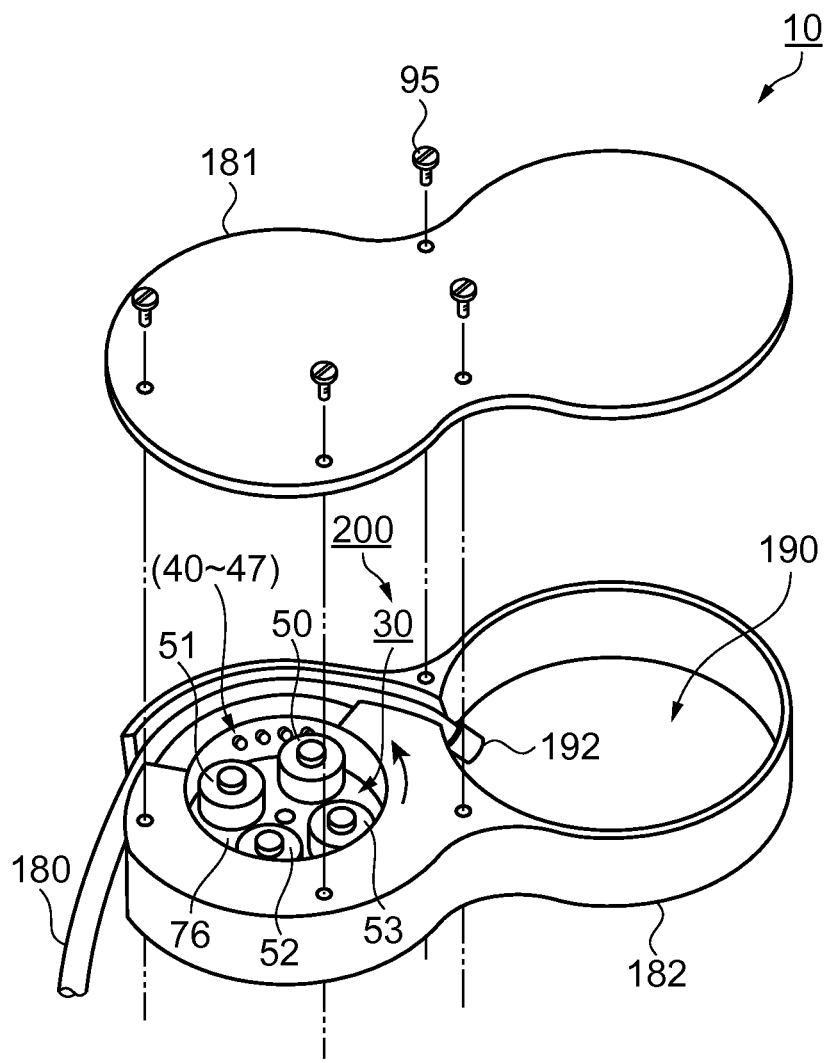
FIG. 7 is a perspective view showing a fluid transporter according to Mode of Embodiment 3 of the invention.

FIG. 7 is an exploded perspective view showing the fluid transporter according to Mode of Embodiment 3. The description is made by designating the portions common to Modes of Embodiment 1 and 2 by the common reference numerals. As shown in FIG. 7, the fluid transporter 10 is provided with a fluid transporting device portion 200 in the casing of a gourd shape in a top plan view, and a fluid storing portion 190. The casing is constituted of a case 182 corresponding to the lower cover of Modes of Embodiment 1 and 2, and an upper cover 181, which are fastened and fixed by the fixing screws 95 (four in FIG. 7).

In the case 182, there are formed two parallel recesses, one of which is provided with the pump unit 30 and the (not-shown) pump drive unit, and the other of which is provided with a fluid storing portion 190. The fluid storing portion 190 and the pump unit 30 are made to communicate with each other by a tube 180. The tube 180 is extended at its one end portion 192 to the fluid storing portion 190, at its midway through the outer circumference portion of the pump unit 30, and at its other end portion to the outside of the fluid transporter 10.

The pump unit 30 adopts the same structure as that of the aforementioned Mode of Embodiment 1 and Mode of Embodiment 2, in which the fluid is transported by the writhing motions of the push pins 40 to 47 (as referred to FIGS. 2 to 6).

The communication among one end portion 192 of the tube 180, the case 182 and the upper cover 181 is provided with the not-shown packing thereby to prevent the fluid from leaking from the fluid storing portion 190 to the inside of the pump unit 30. The fluid storing portion 190 is desirably provided with an opening to be closed with an air-permeable film or the like so that it establishes a pressure substantially equal to that of the ambient pressure when the upper cover 181 is mounted.

Here, the upper cover 181 and the case 182 may be fixed not only by means of the screws but also by adhering means such as solvent weld or adhesion.

According to Mode of Embodiment 3 thus far described, therefore, the pump unit 30 and the fluid storing portion 190 are arranged to have no overlap, so that the size can be reduced without increasing the thickness. Moreover, the casings for the pump unit 30 and the fluid storing portion 190 are formed into one, so that the cost can be reduced.

Here, the invention should not be limited to the foregoing mode of embodiments, but could contain modifications and improvements within the scope to achieve the object of the invention.

In Mode of Embodiment 1 to Mode of Embodiment 3 thus far described, for example, the fluid flow rate (or the transportation rate) can be set by setting the number of rollers, the number of push portions of the rotary disc and so on arbitrarily. However, the rotating speed of the rotary disc 76 can also be selected by storing the not-shown drive control circuit with a plurality of pieces of information capable of selecting the rotating speed arbitrarily. Moreover, the fluid can also be intermittently fed by storing the rotary disc 76 with the information for the intermittent drive.

According to Mode of Embodiment 1 to Mode of Embodiment 3 thus far described, therefore, it is possible to provide both a thin, small fluid transporting device, which can retain a stable fluid feeding rate, and a fluid transporter which is provided with the fluid transporting device.

The invention claimed is:

1. A fluid transporting device, comprising:
   an elastic tube;
   a tube frame that holds the elastic tube in an arc;
   a plurality of push pins disposed on one side of the elastic tube; and
   a rotary push plate arranged for facilitating fluid flow inside the elastic tube from an inlet to an outlet by pushing the plurality of push pins sequentially, the rotary push plate including;
   a plurality of protrusions that place a bias on the elastic tube by pushing the plurality of push pins sequentially; and
   a recess disposed between the plurality of protrusions that releases the bias from the elastic tube,
   wherein the push pins each include:
     a rounded shaped end portion that contacts the rotary push plate; and
     a pushing end portion that places the bias on the elastic tube; and
   each of the protrusions includes an arc that merges into a first slope that terminates at an outer circumference arc that contacts the rounded shaped end portion of the push pin, and a second slope that extends away from the outer circumference arc.

2. A fluid transporting device as set forth in claim 1, wherein
   a material of a case of the fluid transporting device has an organic matching property.

3. A fluid transporting device as set forth in claim 1, wherein
   at least one of the push pins places the bias on the elastic tube.

4. A fluid transporting device as set forth in claim 1, further comprising:
   a fluid storing container coupled to the elastic tube.

5. A fluid transporting device, comprising:
   an elastic tube;
   a tube frame that holds the elastic tube in an arc;
   a plurality of push pins disposed on one side of the elastic tube; and
   a rotary push plate arranged on an upper side of a rotary disc for facilitating fluid flow inside the elastic tube from an inlet to an outlet by pushing the plurality of push pins sequentially, the rotary push plate including:

a plurality of protrusions that place a bias on the elastic tube by pushing the plurality of push pins sequentially, each of the protrusions being non-symmetrical when viewed in plan such that each protrusion includes an arc that merges into a first slope that terminates at an outer circumference arc, which contacts a rounded shaped end portion of each push pin, and a second slope that extends away from the outer circumference arc; and a recess disposed between the plurality of protrusions that releases the bias from the elastic tube, wherein the push pins each include a pushing end portion that places the bias on the elastic tube.

6. The fluid transporting device as set forth in claim 5, wherein a material of a case of the fluid transporting device has an organic matching property.

7. The fluid transporting device as set forth in claim 5, wherein at least one of the push pins places the bias on the elastic tube.

8. The fluid transporting device as set forth in claim 5, further comprising a fluid storing container coupled to the elastic tube.

* * * * *